(12) United States Patent
Weiser (10) Patent No.: US 6,642,017 B2
(45) Date of Patent: Nov. 4, 2003

(54) MODULATING PRODUCTION OF PNEUMOCOCCAL CAPSULAR POLYSACCHARIDE

(75) Inventor: Jeffrey N. Weiser, Merion, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 289 days.

(21) Appl. No.: 09/831,184

(22) PCT Filed: Mar. 16, 2001

(86) PCT No.: PCT/US01/08442
§ 371 (c)(1),
(2), (4) Date: Jan. 30, 2002

(87) PCT Pub. No.: WO01/68903
PCT Pub. Date: Sep. 20, 2001

(65) Prior Publication Data
US 2003/0021811 A1 Jan. 30, 2003

Related U.S. Application Data

(60) Provisional application No. 60/189,847, filed on Mar. 16, 2000.

(51) Int. Cl.[7] ............................. C12Q 1/04; C12Q 1/02; C12Q 1/14; C12Q 1/00
(52) U.S. Cl. ............................. 435/34; 435/29; 435/36; 435/4
(58) Field of Search ............................. 435/34, 29, 36, 435/4

(56) References Cited

FOREIGN PATENT DOCUMENTS

WO    WO 200168903 A1 * 9/2001

OTHER PUBLICATIONS

Chen, Jau–Der and Donald A. Morrison, "Construction and properties of a new insertion vector, pJDC9, that is protected by transcriptional terminators and useful for cloning of DNA from *Streptococcus pneumoniae*." Gene 64: 155–164 (1988).

Auzat, Isabelle, et al., "The NADH oxidase of *Streptococcus pneumoniae*: its involvement in competence and virulence." Molecular Microbiology 34(5): 1018–1028 (1999).

Arrecubieta, Carlos, et al., "Sequence and transcriptional analysis of a DNA region involved in the production of capsular polysaccharide in *Streptococcus pneumoniae* type 3." Gene 167: 1–7 (1995).

Modde, H., "Etude de l'influence de la tension d'$O_2$ de $CO_2$ et de l'anaerobiose sur la morphologie et le nombre des colonies de pneumocoque—Influence of $O_2$–, $CO_2$–tension and anaerobiosis upon number and morphology of pneumococcal colonies." Experientia 34/10: 1285–1286 (1978).

Avery, M.D., Oswald T., and Rene Dubos, Ph.D., "The Protective Action of a Specific Enzyme Against Type III Pneumococcus Infection in Mice." The Journal of Experimental Medicine 54: 73–90 (1931).

(List continued on next page.)

*Primary Examiner*—Louise N. Leary
(74) *Attorney, Agent, or Firm*—Dann, Dorfman, Herrell and Skillman (57) ABSTRACT

The invention relates to methods of modulating capsular polysaccharide production in pneumococci such as *Streptococcus pneumoniae*. The invention further relates to methods of alleviating pneumococcal infections in animals, and to methods of identifying both agents capable of modulating pneumococcal capsular polysaccharide biosynthesis and agents useful for alleviating pneumococcal infections in animals.

26 Claims, 5 Drawing Sheets

OTHER PUBLICATIONS

Knecht, Ph.D., Judith C., et al., "Some Biological Properties of Pneumococcus Type 37 and the Chemistry of its Capsular Polysaccharide." 475–487 (1970).

Avery, Oswald T., et al., "Studies on the Chemical Nature of the Substance Inducing Transformation of Pneumococcal Types." from the Hospital of The Rockerfeller Institute for Medical Research: 137–157 (1943).

MacLeod, Colin M. and Marjorie R. Krauss, "Relation of virulence of pneumococcal strains for mice to the quantity of capsular polysaccharide formed in vitro." From the Department of Microbiology, New York University College of Medicine and College of Denistry, New York: 1–9 (1950).

Caparon, Michael G., et al., "Environmental Regulation of Virulence in Group A Streptococci: Transcription of the Gene Encoding M Protein Is Stimulated by Carbon Dioxide." Journal of Bacteriology: 5693–5701 (1992).

Weiser, Jeffrey N., "Phase Variation in Colony Opacity by *Streptococcus pneumoniae*." Microbial Drug Resistance 4(2): 129–135 (1998).

Weiser, Jeffrey N. and Miki Kapoor, "Effect of Instrastrain Variation in the Amount of Capsular Polysaccharide on Genetic Transformation of *Streptococcus pneumoniae*: Implications for Virulence Studies of Encapsulated Strains." Infection and Immunity: 3690–3692 (1999).

Watson, David A. and Daniel M. Musher, "Interruption of Capsule Production in *Streptococcus pneumoniae* Serotype 3 by Insertion of Transposon Tn916." Infection and Immunity 58(9): 3135–3138 (1990).

Weiser, Jeffrey N., et al., "Phase Variation in Pneumococcal Opacity: Relationship between Colonial Morphology and Nasopharyngeal Colonization." Infection and Immunity 62(6): 2582–2589 (1994).

Gibson, Ronald L., et al., "Group B Streptococci Invade Endothelial Cells: Type III Capsular Polysaccharide Attenuates Invasion." Infection and Immunity 61(2): 478–485 (1993).

St. Geme III, Joseph W. and Stanley Falkow, "Loss of Capsule Expression by *Haemophilus influenzae* Type b Results in Enhanced Adherence to and Invasion of Human Cells." Infection and Immunity 59(4): 1325–1333 (1991).

Kim, Jean O., et al., "Relationship between Cell Surface Carbohydrates and Intrastrain Variation on Opsonophagocytosis of *Streptococcus pneumoniae*." Infection and Immunity 67(5): 2327–2333 (1999).

Tuomanen, M.D., Elaine I., et al., "Pathogenesis of Pneumococcal Infection." The New England Journal of Medicine 332(19): 1280–1284 (1995).

Saluja, Sunil K. and Jeffrey N. Weiser, "The genetic basis of colony opacity in *Streptococcus pneumoniae*: evidence for the effect of box elements on the frequency of phenotypic variation." Molecular Microbiology 16(2): 215–227 (1995).

Sellin, Mats, et al., "Phase-shift of polysaccharide capsule expression in group B streptococci, type III." Microbial Pathogenesis 18: 401–415 (1995).

Ring, Axel, et al., "Pneumococcal Traficking across the Blood–Brain Barrier Molecular Analysis of a Novel Bidirectional Pathway." J. Clin. Invest. 102(2): 347–360 (1998).

Iannelli, Francesco, et al., "The Type 2 Capsule Locus of *Streptococcus pneumoniae*." Journal of Bacteriology 181(8): 2652–2654 (1999).

Levin, James C. and Michael R. Wessels, "Identification of *csrR/csrS*, a genetic locus that regulates hyaluronic acid capsule synthesis in group A *Streptococcus*." Molecular Microbiology 30(1): 209–219 (1998).

Ilan, Ofir, et al., "Protein tyrosine kinases in bacterial pathogens are associated with virulence and production of exopolysaccharide." The EMBO Journal 18(12): 3241–3248 (1999).

Vincent, Carole, et al., "Cells of *Escherichia coli* Contain a Protein–Tyrosine Kinase, Wzc, and a Phosphotyrosine–Protein Phosphatase, Wzb." Journal of Bacteriology 181(11): 3472–3477 (1999).

Throup, John P., et al., "A genomic analysis of two–component signal transduction in *Streptococcus pneumoniae*." Molecular Microbiology 35(3): 566–576 (2000).

Rosenow, Carsten, et al., "Contribution of novel choline–binding proteins to adherence, colonization and immunogenicity of *Streptococcus pneumoniae*." Molecular Microbiology 25(5): 819–829 (1997).

Raz, Raul, et al., "Pneumococcal Bacteremia in Hospitalized Israeli Adults: Epidemiology and Resistance to Penicillin." Clinical Infectious Diseases 24: 1164–8 (1997).

Kim, Jean O. and Jeffrey N. Weiser, "Association of Intrastrain Phase Variation in Quantity of Capsular Polysaccharide and Teichoic Acid with the Virulence of *Streptococcus pneumoniae*." The Journal of Infectious Diseases 177: 368–77 (1998).

Schrager, Harry M., et al., "Hyaluronic Acid Capsule and the Role of Streptococcal Entry into Keratinocytes in Invasive Skin Infection." J. Clin. Invest. 98(9): 1954–1958 (1996).

Wani, Javaid H., et al., "Identification, Cloning, and Sequencing of the Immunoglobulin A1 Protease Gene of *Streptococcus pneumoniae*." Infection and Immunity: 3967–3974 (1996).

Stevenson, Gordon., et al., "Organization of the *Escherichia coli* K–12 Gene Cluster Responsible for Production of the Extracellular Polysaccharide Colanic Acid." Journal of Bacteriology: 4885–4893 (1996).

Hammerschmidt, Sven, et al., "Capsule phase variation in *Neisseria meningitidis* serogroup B by slipped–strand mispairing in the polysialytransferase gene (*siaD*): correlation with bacterial invasion and the outbreak of meningococcal disease." Molecular Microbiology 20(6): 1211–1220 (1996).

Cundell, Diana R., et al., "*Streptococcus pneumoniae* anchor to activated human cells by the receptor for platelet–activating factor." Nature 377: 435–438 (1995).

Austrian, Robert and Patricia Collins, "Importance of Carbon Dioxide in the Isolation of Pneumococci." Journal of Bacteriology 92(5): 1281–1284 (1996).

Tomasz, Bacteriol. Proc. 64: 29G87 (1964).

* cited by examiner

Fig. 1Ai         Fig. 1Aii        Fig. 1Aiii

Fig. 1Bi         Fig. 1Bii        Fig. 1Biii

MODULATING PRODUCTION OF PNEUMOCOCCAL CAPSULAR POLYSACCHARIDE

This application is a 371 of PCT/US01/08442, filed Mar. 16, 2001 which claims benefit of 60/189,847, filed Mar. 16, 2000.

This research was supported in part by U.S. Government funds (U.S. Public Heath Service grant numbers AI38436 and AI44231), and the U.S. Government may therefore have certain rights in the invention.

BACKGROUND OF THE INVENTION

The invention relates broadly to production of capsular polysaccharide material from streptococcal organisms and to production of vaccines using such material.

*Streptococcus pneumoniae*, sometimes designated pneumococcus, is generally a commensal organism colonizing the mucosal surface of the human nasopharynx. When host factors allow the organism access to the lower respiratory tract, a vigorous inflammatory response ensues, leading to a dense consolidation as alveolar air spaces fill with exudate. This condition is commonly referred to as pneumonia (Tuomanen et al., 1995). The most serious manifestation of pneumococcal infection is bacteremia, which can be complicated by sepsis, meningitis, or both. Bacteremia in adults is usually a complication of pneumonia (Raz et al., 1997).

The ability of the pneumococcus to resist the major mechanism of clearance of the organism from the bloodstream (i.e. opsonophagocytosis) requires expression of the major virulence factor of the organism, which is a polysaccharide capsule (Avery et al., 1931; Watson et al., 1990). Pneumococci are capable of synthesizing no fewer than 90 structurally unique capsular polysaccharides (CPSs).

Pneumococcal CPS exhibits anti-phagocytic properties and inhibits adherence to host cells, a critical step in carriage (i.e. spread of the organism from one infected, but not necessarily symptomatic, individual to another) and possibly later aspects in the pathogenesis of disease (Ring et al., 1998). Similar findings in other encapsulated species (e.g. *Haemophilus influenzae, Neisseria meningitidis, Streptococcus pyogenes,* and *Streptococcus agalactiae*) has led to an appreciation of how amounts of CPS must be temporally varied to allow both adhesive interactions with host cells and resistance to humoral immunity (Hammerschmidt et al., 1996; Levin et al., 1998; Schrager et al., 1996; Sellin et al., 1995; St. Geme III et al., 1991).

Even within a single strain, the amount of CPS expressed by *S. pneumoniae* varies. The regulatory mechanism(s) which modulate CPS expression have not previously been well understood. Most pneumococcal isolates undergo phenotypic variation between at least two forms, which can be distinguished by colony opacity (Weiser, 1998; Weiser et al., 1994). Opaque (O) colony forms differ from transparent (T) variants of the same strain in the amount of CPS that is synthesized, O-form colonies generally making a greater amount of CPS (Kim et al., 1998).

Relatively minor differences in the amount of CPS made by a pneumococcal variant can have a major impact on virulence (MacLeod et al., 1950). The 1.2 to 5.6-fold higher quantities of CPS produced by O-form colonies, compared to T-form colonies, correlates with increased resistance of pneumococcal cells to opsonophagocytosis using immune serum (Kim et al., 1999). In a murine model of systemic infection, only the O variant of several pneumococcal strains caused sepsis (Kim et al., 1998). In contrast, the T form expresses higher amounts of the other cell surface polysaccharide, teichoic acid. Pneumococcal cell-wall teichoic acid is covalently linked to CPS and contains an unusual host-like constituent, phosphorylcholine. This polysaccharide contributes to adherence of pneumococcal cells to epithelial cells via the receptor for platelet activating factor (Cundell et al., 1995; Cundell et al., 1995; Kim et al., 1998). The T form also exhibits an altered distribution of cell surface choline-binding proteins, including CbpA, which acts to promote adherence and colonization (Rosenow et al., 1997). During carriage in an infant rat model, there is selection for pneumococcal variants which exhibit the T, rather than O, phenotype (Weiser et al., 1994). These observations suggests that pneumococci vary between a form (i.e. the T-form) which exhibits greater adherence and carriage, and a non-adherent form (i.e. the O-form) which is better adapted to survival in invasive infection.

Identification of the CPSs expressed by a pneumococcus forms the basis of serotyping, a diagnostic procedure used for differentiating *S. pneumoniae* variants. Because different variants can exhibit different physiological properties (e.g. susceptibility to anti-microbial agents or characteristic rate of onset or progression of pneumonia), ability to differentiate pneumococcal variants is medically advantageous. Furthermore, because the ability of the human (or other vertebrate) immune system to recognize and attack pneumococcal variants depends on its ability to specifically recognize the CPS of each variant, ability to obtain pneumococcal variant-specific CPS significantly affects development of therapeutic and preventive methods and compositions for alleviating disorders associated with pneumococcal infection. For example, known pneumococcal vaccines comprise CPS obtained from numerous pneumococcal variants.

There remains a significant need for diagnostic, prognostic, therapeutic, and preventive compositions and methods useful with disorders associated with pneumococcal infection. Many of these compositions and methods comprise, employ, or rely for their development on isolated pneumococcal CPS. Previously known methods for isolating CPS from pneumococci are generally characterized by low yield. The present invention includes a method of improving the yield of CPS that can be obtained from a pneumococcal variant, and enhances production and use of diagnostic, prognostic, therapeutic, and preventive compositions and methods pertaining to pneumococcal infections.

BRIEF SUMMARY OF THE INVENTION

The invention relates to an improvement in a method of producing capsular polysaccharide from a pneumococcus by maintaining the pneumococcus in a growth medium. In one aspect, the improvement comprises maintaining a gas having a sub-atmospheric concentration of oxygen in contact with the growth medium (e.g. an oxygen concentration not greater than about 16% or not greater than about 0.1%). The pneumococcus can be an organism of the genus Streptococcus, such as an organism of the species *Streptococcus pneumoniae* (e.g. one of *S. pneumoniae* variants 6A, 6B, 18C, and 9V). In another aspect, the improvement comprises maintaining a gas having a super-atmospheric concentration (e.g. at least about 3% or 10%) of carbon dioxide in contact with the growth medium. In a third aspect, the improvement comprises maintaining a gas having both a super-atmospheric concentration of carbon dioxide and a sub-atmospheric concentration of oxygen in contact with the growth medium. In still another aspect, the improvement comprises maintaining the carbon dioxide concentration of the growth medium at a level at least equal to the concentration of carbon dioxide in the same growth medium equilibrated at the same temperature with a gas comprising 5% carbon dioxide.

The invention also relates to a method of alleviating a pneumococcal infection in an animal. This method comprises maintaining the animal (e.g. at least the lungs of the animal) in contact with a gas having a super-atmospheric concentration (e.g. 25%, 50%, or 100%) of oxygen. Examples of infections which can be alleviated in this method include pneumonia, bacteremia, sepsis, and meningitis.

The invention further relates to a method of making an immunogenic preparation for administration to an animal at risk for developing a pneumococcal infection. This method comprises maintaining pneumococcal cells in a growth medium having an oxygen content lower than the same medium equilibrated at the same temperature with normal air and isolating capsular polysaccharide produced by the cells from the cells. The isolated polysaccharide constitutes the immunogenic preparation.

The invention still further relates to a method of producing pneumococcal polysaccharide. This method comprises maintaining pneumococcal cells in a growth medium having an oxygen content lower than the same medium equilibrated at the same temperature with normal air, for example, a medium substantially devoid of oxygen. In one embodiment, the medium has a carbon dioxide content which is greater than the same medium equilibrated at the same temperature with normal air, for example, a medium saturated with carbon dioxide or a medium comprising a carbonate or bicarbonate salt.

The invention includes a method of assessing whether a test compound is useful for alleviating a pneumococcal infection in an animal. This method comprises comparing (a) the degree of phosphorylation of CpsD in pneumococcal cells maintained in the presence of the test compound and (b) the degree of phosphorylation of CpsD in the same type of cells maintained in the absence of the test compound. If the degree of phosphorylation of CpsD in the cells maintained in the presence of the test compound is less than the degree of phosphorylation of CpsD in the cells maintained in the absence of the test compound, then the test compound is useful for alleviating the infection. The degree of phosphorylation of CpsD can, for example, be assessed by assessing the number of phosphorylated tyrosine residues present in CpsD or by assessing the fraction of CpsD having at least one phosphorylated tyrosine residue.

BRIEF DESCRIPTION OF THE DRAWINGS

FIG. 2, comprising FIGS. 2A–2D, is a quartet of bar graphs which depict the effects of environmental oxygen and carbon dioxide concentration and opacity phenotype on CPS production, on a per unit protein basis, as assessed using a capture ELISA. Opaque (FIGS. 2Ai, 2Bi, 2Ci, and 2Di) and transparent (FIGS. 2Aii, 2Bii, 2Cii, and 2Dii) variants of isolates of the four pneumococcal types (variant 6B in FIGS. 2Ai and 2Aii; variant 6A in FIGS. 2Bi and 2Bii; variant 18C in FIGS. 2Ci and 2Cii; variant 9V in FIGS. 2Di and 2Dii) were grown to mid-log phase (solid bars) or stationary phase (stippled bars) at oxygen and carbon dioxide concentrations indicated above the graphs. CPS production was determined in sonicated cell pellets and in culture supernatants (hatched bars), and is expressed relative to the quantity of total cellular protein. "*" indicates that this variant did not grow under this condition. Values represent the mean of two separate experiments in duplicate.

FIG. 3, comprising FIGS. 3A and 3B, is a pair of images which depict the effects of environmental oxygen and carbon dioxide concentration and opacity phenotype on tyrosine phosphorylation of CpsD in Western analysis. Whole cell lysates of O (lanes 1–4) and T (lanes 5–8) forms of pneumococcal variant P303 were removed after growth on solid medium and adjusted to equal density. The image in FIG. 3A depicts proteins in these samples which were separated by SDS-PAGE, transferred to a membrane, and immunoblotted with a monoclonal antibody designated 4G10, which binds specifically with phosphorylated tyrosine. The image in FIG. 3B depicts duplicate membranes which were immunoblotted using antisera raised against whole pneumococci in order to demonstrate equal loading. Growth conditions corresponding to the cells lysed and applied to lanes were as follows: in lanes 1 and 5, <0.1% $O_2$/10% $CO_2$; in lanes 2 and 6, 16% $O_2$/3% $CO_2$; in lanes 3 and 7, 21% $O_2$/<0.1% $CO_2$; and in lanes 4 and 8, 19% $O_2$/10% $CO_2$. The arrow in FIG. 3A indicates the location of the 25 kD CpsD band. Size markers are in kilodaltons.

DETAILED DESCRIPTION OF THE INVENTION

The invention relates to the discovery by the inventor that the amount of capsular polysaccharide (CPS) produced by pneumococci can be modulated by controlling the oxygen and carbon dioxide content of the medium in which they are maintained. It has also been discovered by the inventor that CPS production in *Streptococcus pneumoniae* is modulated by the presence of CpsD protein and by the post-translational modification of this protein. Based on these discoveries, the present invention includes methods for modulating CPS production by pneumococci (e.g. for use in production of anti-pneumococcal vaccines and other immunogenic preparations), methods for alleviating pneumococcal infections, and methods of identifying agents useful for alleviating pneumococcal infections.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Normal" air refers to a gas having approximately the average content of the atmosphere at a selected location, without regard to the humidity (i.e. on a dry basis). The average content of the atmosphere is about 78% $N_2$, 21% $O_2$, 1% Ar, and less than 0.04% each of $CO_2$, $H_2$, He, Ne, Kr, and Xe.

Description

It has been discovered that production of capsular polysaccharide (CPS) by pneumococci is influenced by the presence and concentration of oxygen and carbon dioxide present in the cells' environment. In particular, production of CPS increases as the oxygen content of the environment decreases; production of CPS also increases as the carbon dioxide content of the environment increases. Although these observations have been made using cultures of *Streptococcus pneumoniae*, they can also be applied to organisms which exhibit capsule and capsule gene properties similar to pneumococci, such as other Streptococcus species (e.g. *Streptococcus agalactiae*), to other encapsulated organisms such as *Staphylococcus aureus, Klebsiella pneumoniae,* and *Acinetobacter johnsonii*, and organisms which exhibit phenotypic similarity, genotypic similarity, or both, to one or more of these. When the organism is *Streptococcus pneumoniae*, it can be any known or hereafter discovered variant thereof, including variants characterized by the identity of their CPS, such as one of variants 6A, 6B, 18C, and 9V.

These observations can be used in conjunction with any known method of culturing pneumococci, or with any method hereafter developed, to increase (or decrease, if desired) production of CPS by pneumococci cultured by such methods. The invention includes a method of increasing the yield of CPS obtained by culturing a pneumococcus according to a known method. The improved method involves decreasing the oxygen content of the medium in or on which the pneumococcus is maintained, relative to the oxygen content which normally occurs in the medium during culture of the pneumococcus. For example, it is common to culture pneumococcus on a gelatinous or semi-solid medium or in a liquid medium, wherein the medium is maintained in contact with filtered (or otherwise sterilized) normal air.

Production of CPS by pneumococci can be increased by decreasing (on a dry basis) the oxygen content of the gas with which the medium is maintained in contact. The degree to which the oxygen content is decreased is not critical, but, generally speaking, the greater the decrease in oxygen content is, the greater the increased yield of CPS will be. The oxygen content of the gas is preferably <16%, or is decreased to the point that the gas is substantially anaerobic (e.g. such that it contains <0.1% $O_2$). The manner in which the oxygen content of the gas is decreased is not critical. Convenient methods of reducing the oxygen content of the gas below the oxygen content of normal air include flushing the culture vessel (at least initially, but alternatively intermittently, periodically, or continuously) with a gas having the desired oxygen content. For example, a culture vessel can be flushed with a gas mixture comprising about 71% $N_2$, 19% $O_2$, and 10% $CO_2$, or with a mixture comprising 95% Ar and 5% $CO_2$.

Production of CPS by pneumococci can also be increased by increasing the carbon dioxide content of the gas with which the medium on or in which the pneumococci are maintained is contacted. The degree to which the carbon dioxide content of the gas is increased is not critical, but, generally speaking, the greater the increase in carbon dioxide content is, the greater the increased yield of CPS will be. The carbon dioxide content of the gas is preferably at least about 5%, or at least about 10%, although it can be so high that the culture medium is saturated with carbon dioxide. As discussed above, the desired carbon dioxide content can be achieved by flushing the vessel in which the pneumococci are cultured with a gas having the desired carbon dioxide content. Alternatively, carbon dioxide can be provided to the medium by incorporating a carbonate or bicarbonate salt into the medium or by adding such as salt to the medium.

The invention includes methods of increasing CPS production by pneumococci by increasing the carbon dioxide content of the medium in which the pneumococci are maintained, by increasing the carbon dioxide content of a gas which contacts that medium, by decreasing the oxygen content of that medium, by decreasing the oxygen content of a gas which contacts that medium, or any combination of these. In one embodiment, the $O_2/CO_2$ content of the medium (or of a gas in contact with the medium) can be adjusted so as to maximize the yield of pneumococcal cells during one phase, and then can be re-adjusted to maximize production of CPS during a second phase.

Decreasing the oxygen content of the gas which contacts the medium causes a decrease in the oxygen content of the medium on or in which the pneumococcus is maintained, owing to equilibration of dissolved and non-dissolved gas. Changing the carbon dioxide content of the gas has a similar effect. The rapidity with which the gas dissolved in the medium and non-dissolved gas equilibrate depends on a number of factors known in the art, including, for example, the surface area of the medium-gas interface, the viscosity of the medium, and the degree of agitation of the medium.

Pneumococci can be maintained in medium (e.g. liquid medium) in which the interface between the medium and any gas phase, if any, is minimized. In such culture systems, altering the content of the gas phase can have relatively little effect on the gas content of the liquid medium, owing to limited diffusion of gas from the gas phase into the liquid. In such systems, the gas content of the liquid medium can be influenced by the method used to prepare the medium. For example, substantially anaerobic liquid medium can be made by preparing a liquid medium, sterilizing it in an autoclave (the heat of which drives substantially all oxygen from the liquid), and cooling the autoclaved medium in an oxygen-free atmosphere, such as in a closed container through which a steady stream of oxygen-free gas is passed. Examples of suitable oxygen-free gases include pure argon, argon mixed with 5–10% $CO_2$, pure nitrogen, or some combination of $N_2$, Ar, and $CO_2$. Where a very high degree of anaerobicity is desired ($[O_2]<<0.1\%$), the oxygen-free gas which passes over the medium as it cools can be passed through or over a heated copper coil or mesh, using methods known in the art. Of course, similar methods can be used for preparation of solid, gelatinous, and semi-solid media having a desired gas content.

CPS production can also be enhanced by selecting an appropriate pneumococcal variant and form as the inoculum used to seed the medium for which the oxygen content, carbon dioxide content, or both, is modulated. It is understood that different variants of pneumococci can generate structurally distinct CPS. The methods described herein can be used to enhance CPS production using any pneumococcal variant. It is furthermore understood that many pneumococci exhibit at least two phenotypic forms. These forms can include an opaque (O) form and a transparent (T) form, wherein the opaque form is generally characterized by producing a greater amount of CPS. Thus CPS production can be further enhanced by selecting, as an inoculum, a form of a variant of a pneumococcus characterized by greater CPS production.

CPS produced using one or more of the methods described herein can be used (alone or in combination with other pneumococcal CPS species) to make pneumococcal vaccines and other immunogenic preparations using methods known in the art. Such methods generally involve separating the CPS from pneumococcal cells, optionally killing remaining pneumococcal cells, and combining the CPS with a pharmaceutically acceptable carrier (and, optionally, an immunological adjuvant). Such preparations can be administered to an animal for the purpose of enhancing the immune response of the animal to infection by a pneumococcus.

Because pneumococcal CPS is believed to enable pneumococci to elude immune defenses in animals (e.g. humans), methods of inhibiting CPS production can be used to alleviate pneumococcal infections in animals. Pneumococcal infections (and complications arising therefrom) which can be alleviated in this manner include pneumonia (particularly pneumococcal pneumonia), bacteremia, sepsis, meningitis bacterial endocarditis, streptococcal exudative pharyngitis, cellulitis, and visceral abscesses.

It has been discovered that increasing the oxygen content in the environment decreases pneumococcal CPS production, thereby increasing the susceptibility of the pneumococci to the immune system. Similarly, it has been discovered that decreasing the carbon dioxide content in the environment decreases pneumococcal CPS production.

Pneumococcal infections and their side effects and complications can be alleviated by maintaining an animal afflicted with such an infection in contact with a gas having a super-atmospheric concentration of oxygen. Alternatively, the oxygen tension at the site of the infection can be increased (e.g. by providing pure oxygen or sterilized air directly to an infection site {e.g. a visceral abscess involving a pneumococcus} located within an animal body), relative to the normal oxygen tension at the site. For example, when the body site is the lungs (e.g. as with pneumococcal pneumonia), the normal oxygen tension is that of normal air. Pneumococcal pneumonia can be alleviated by providing a supra-atmospheric concentration of oxygen to the patients lungs using, for example, a respirator or a standard oxygen mask.

Pneumococcal infections and their side effects and complications can also be alleviated by decreasing the carbon dioxide tension at the site of infection in an animal below the carbon dioxide tension that normally occurs at such infection sites, and preferably below the carbon dioxide tension that normally occurs at that body site, even in the absence of pneumococcal infection. Decreasing the carbon dioxide tension at an internal body site other than the lungs can involve providing a flow of sterile gas through, over, or past the body site. When the site of infection is the lungs, carbon dioxide tension can be reduced by increasing the respiration rate, either by voluntary action of the patient or artificially (e.g. using a ventilator or respiration-quickening drugs).

As described in greater detail in the example, increased CPS production in pneumococci is correlated with low expression of the cpsD gene and with a low degree of phosphorylation of CpsD protein. Production of CPS can therefore be enhanced by agents which increase expression of cpsD, increase the degree of phosphorylation of CpsD, or both. Conversely, production of CPS can be inhibited by agents which inhibit or reduce expression of cpsD, inhibit phosphorylation of CpsD, enhance de-phosphorylation of phosphorylated CpsD, or some combination of these. As discussed above, decreasing production of CPS in pneumococci involved in an infection in an animal can render those pneumococci more susceptible to attack by the animal's immune system.

The invention includes methods of assessing whether a test compound is an inhibitor of pneumococcal CPS production and methods of assessing whether a test compound is an enhancer of pneumococcal CPS production. In each of these methods, pneumococcal cells are maintained in the presence of the test compound and, separately but preferably identically, in the absence of the test compound. A direct effect of the test compound on CPS production can be assessed by assessing the amount of CPS produced by cells in the presence and absence of the test compound. Alternatively, the level of expression of cpsD (assessed by measuring production of either the corresponding RNA or the corresponding protein) or the degree of phosphorylation of CpsD (assessed by measuring either the number of phosphorylated tyrosine residues present in CpsD or the fraction of CpsD having at least one phosphorylated tyrosine residue) is assessed, and correlated with inhibition or enhancement of CPS production, as discussed above.

References

Publications referred to in this application are as follows.
Arrecubieta et al., 1995, Gene 167:1–7
Austrian et al., 1966, J. Bacteriol. 92:1281–1284
Auzat et al., 1999, Mol. Microbiol. 34:1018–1028
Avery et al., 1931, J Exp. Med. 54:73
Avery et al., 1944, J Exp. Med. 79:137–157
Caparon et al., 1992, J. Bacteriol. 174:5693–5701
Chen et al., 1988, Gene 164:155–164
Cundell et al., 1995, Nature 377:435–438
Cundell et al., 1995, Infect. Immun. 63:757–761
Gibson et al., 1993, Infect. Immun. 61:478–485
Hammerschmidt et al., 1996, Mol. Microbiol. 20:1211–1220
Howden, 1976, J. Clin. Pathol. 29:50–53
Iannelli et al., 1999, J. Bacteriol. 181:2652–2652
Ilan et al., 1999, EMBO J. 18:3241–3248
Kim et al., 1998, J. Infect. Dis. 177:368–377
Kim et al., 1999, Infec. Immun. 67:2327–2333
Knecht et al., 1970, J. Exp. Med. 132:475–487
Levin et al., 1998, Mol. Microbiol. 30:209–219
MacLeod et al., 1950, J. Exp. Med. 92:1–9
Modde, 1978, Experimentia 34:1285–1286
Neufeld, 1902, Z. Hyg. Infektionskr. 40:54
Raz et al., 1997, Clin. Infect. Dis. 24:1164–1168
Ring et al., 1998, J. Clin. Invest. 102:347–360
Rosenow et al., 1997, Mol. Microbiol. 25:819–829
Saluja et al., 1995, Mol. Microbiol. 16:215–227
Schrager et al., 1996, J. Clin. Invest. 98:1954–1958
Sellin et al., 1995, Microb. Pathogen. 18:401–415
St. Geme III et al., 1991, Infect. Immun. 59:1325–1333

Stevenson et al., 1996, J. Bacteriol. 178:4885–4893
Throup et al., 2000, Mol. Microbiol. 35:566–576
Tomasz, 1964, Bacteriol. Proc. 64:29
Tuomanen et al., 1995, New Eng. J. Med. 332:1280–1284
Vincent et al., 1999, J. Bacteriol. 181: 3472–3477
Wani et al., 1996, Infect. Immun. 64:3967–3974 which 5000 units of catalase (obtained from Worthington Biochemical, Freehold, N.J.) was spread. Inoculated media were incubated at 37° C. in a candle extinction jar unless otherwise specified. Colony morphology was determined on this TSA medium under magnification and oblique, transmitted illumination, as described (Weiser et al., 1994).

TABLE I

Reactivity of Pneumococcal Strains and Mutants with a Monoclonal Antibody which Binds Specifically with Phosphotyrosine

| Strain | Encapsulation +/− | type | Mucoidy aerobic | anaerobic | Characteristics/ Genotype | Phenotype[7] Mab 4G10(+/−) | Reference |
|---|---|---|---|---|---|---|---|
| P303 | + | 6A | No | Yes | clinical isolate | + | (Kim et al., 1998) |
| P324 | + | 6B | No | Yes | clinical isolate | + | (Kim et al., 1998) |
| P68 | + | 18C | No | Yes | clinical isolate | + | (Kim et al., 1998) |
| P10 | + | 9V | No | Yes | clinical isolate | + | (Weiser et al., 1994) |
| D39 | + | 22 | No | Yes | clinical isolate | + | (Avery et al., 1944) |
| R6x | − | | No | No | D39(Δcps2A-cps2H) | − | (Iannelli et al., 1999) |
| SIII | + | 3 | Yes | Yes | clinical isolate | − | (Avery et al., 1944) |
| P138 | + | 3 | Yes | Yes | R6x x SIII DNA | − | (Saluja et al., 1995) |
| P728 | + | 2 | No | Yes | R6x x D39 DNA | + | This example |

[7]For each strain/mutant the O phenotype grown in the presence of oxygen was tested. '+', indicates reactivity with a single band of 25–27 kD.

Watson et al., 1990, Infect. Immun. 58:3135–3138
Weiser, 1998, Microb. Drug Resist. 4:129–145
Weiser et al., 1994, Infect. Immun. 62:2582–2589
Weiser et al., 1999, Infect. Immun. 67:3690–3692
Weyand et al., 2000, J. Biol. Chem. 275:3192–3200

EXAMPLE

The invention is now described with reference to the following Example. This Example is provided for the purpose of illustration only, and the invention is not limited to this Example, but rather encompasses all variations which are evident as a result of the teaching provided herein.

Oxygen Dependence of Capsular Polysaccharide Expression by *Streptococcus pneumoniae* is Associated with Post-Translational Modification of CpsD The experiments presented in this Example demonstrate that differences in opacity phenotype among pneumococci (i.e. O-form versus T-form) are affected by environmental concentrations of oxygen, and that anaerobic growth conditions such as may occur in pneumonia influence the ability of O-form pneumococci to increase expression of CPS and evade immune clearance.

The materials and methods used in the experiments presented in this Example are now described.

Bacterial Strain and Growth Conditions

Strains of *S. pneumoniae* used in this study are described in Table I and included previously described O and T variants of clinical isolates P303 (type 6A), P324 (type 6B), P68 (type 18C) and P10 (type 9V), as described (Kim et al., 1998; Weiser et al., 1994). Bacteria were grown in non-sealed vessels in a semi-synthetic (C+Y medium, pH 8.0) or tryptic soy medium without shaking at 37° C., as described (Tomasz, 1964). Broth cultures were plated onto standard tryptic soy agar (TSA) plates containing 1% (w/v) agar, onto Environmental carbon dioxide concentration was controlled under aerobic conditions using a $CO_2$ incubator. Anaerobic growth conditions were obtained using the BBL GasPak™ system according to the manufacturer's instructions (Becton Dickinson, Cockeysville, Md.). In some experiments, the sodium bicarbonate component of the system was employed in order to generate a 10% carbon dioxide atmosphere, and in other experiments, it was not. After harvesting the bacteria, the pH of the growth medium was measured to confirm that it was not affected by these differing culture conditions.

Analysis of clinical specimens was performed using similar methods. A total of 502 patients afflicted with meningitis were examined, of whom approximately 20% had bacteriologically proven pneumococcal meningitis. A nasopharyngeal swab sample was collected from patients in whom a presumptive clinical diagnosis of pneumococcal meningitis had been made. This sample was plated immediately onto both 5% sheep's blood agar and tryptic soy agar containing 5000 units of catalase, and the plates were incubated at 37° C. in an air atmosphere containing 5% $CO_2$. Cerebrospinal fluid (CSF) samples were also plated on both blood agar and transparent plates, as were cultured patient blood samples in which pneumococci were observed following standard aerobic incubation for up to 48 hours. Initially, isolates which exhibited typical morphology on blood agar were confirmed as being pneumococci by Gram stain and Quellung reaction. All isolates were stored at −80° C. in bacterial preservers, and colony morphology was determined as described herein. Statistical differences between rates of T and O phenotypes in nasopharyngeal and invasive site cultures were examined using Fisher's Exact Test.

Genetic Transformation

Encapsulated and non-encapsulated pneumococci were made competent for natural transformation as described (Weiser et al., 1999). Mutations in two-component signal transduction systems (TCSTSs) were transformed into strain P303 by selection of colonies from medium comprising erythromycin (1 microgram per milliliter). Encapsulated transformants were screened for altered colony morphology, and expression of CPS confirmed by the Quellung reaction using type-specific antisera (obtained from Statens Seruminstitut, Copenhagen, Denmark).

Quellung Reaction

Pneumococcal capsules were visualized in bacteria grown to mid-log phase in semi-synthetic medium under various conditions. For the Quellung reaction, an equal volume of culture and a composition comprising type 6 anti-serum and 1% (w/v) methylene blue obtained from the Statens Seruminstitut (Copenhagen, Denmark) were mixed on a glass slide for one minute, as described (Neufeld, 1902).

Quantitation of CPS

O- and T-form pneumococcal variants were grown in the semi-synthetic medium to mid-log phase ($A_{620}=0.3$) or for 16 hours (at which time the cells were in the stationary phase). Cells were harvested by centrifugation at 2000×g, washed in phosphate-buffered saline (PBS), sonicated for three 10-second intervals at 0° C., and stored at −20° C. A capture ELISA technique was used to determine quantities of CPS present in variants grown under selected conditions, as described (Kim et al., 1998). Type-specific rabbit anti-serum (obtained from Statens Seruminstitut, Copenhagen, Denmark) was used at a dilution of 1:5,000 in 0.05 molar $Na_2CO_3$ (pH 9.6), and was fixed overnight at room temperature to the walls of wells in microtiter plates. Between each incubation step, the plate was washed five times with Tris buffer (comprising 10 millimolar Tris, 150 millimolar NaCl, 0.05% Brij™ 35, and 0.02% (w/v) sodium azide). Brij™ 35 (polyoxyethylene(23) lauryl ether $C_{12}H_{25}(OCH_2CH_2)_{23}OH$) is a detergent. Purified CPS obtained from type 6B, 6A, 18C or 9V pneumococci was used at a known concentration, and was purchased from the American Type Tissue Collection (Rockville, Md.) for use as a standard. CPS in sonicated cell samples was detected using monoclonal antibodies designated HASP 4 (which binds specifically with type 6A and 6B CPSs), HASP 22 (which binds specifically with type 18C CPS), and HASP 33 (which binds specifically with type 9V CPS), and were used at a concentration determined in pilot experiments. Binding of monoclonal antibodies and CPS was detected using antisera which reacts specifically with mouse IgM and which is conjugated with alkaline phosphatase. This reagent was used as described (Kim and Weiser, 1998). Total cellular protein determination was carried out with sonicated cell extracts using the micro-bicinchoninic acid kit according to the manufacturer's directions (Pierce Chemical Co., Rockford, Ill.). The amount of CPS in the supernatant fraction was based on protein concentration in the corresponding cell sonicate fraction (i.e. in order to normalize CPS content on a per-unit-protein basis).

The capture ELISA method used to compare amounts of total teichoic acid in cell sonicates has been described (Kim et al., 1998). All experiments were performed in duplicate, and repeated at least three times. Results are expressed as mean values per total cellular protein concentration.

Western Analysis

Bacteria were grown on tryptic soy agar supplemented with catalase as described above. After growth under selected conditions for 16 hours at 37° C., cells were removed from the surface using a sterile Dacron™ swab, re-suspended in PBS, and washed in PBS in order to adjust the cell density such that $A_{620}=0.5$. After centrifuging, pelleted cells were re-suspended in Laemmli gel loading buffer and heated to 100° C. for 5 minutes. The samples were then separated by SDS-PAGE on 12.5% (w/v) polyacrylamide gels, and then transferred to Immobilon-P™ membranes as described (Wani et al., 1996).

Immunoblotting was performed using a monoclonal antibody designated 4G10 (Upstate Biotechnology Inc., Waltham, Mass.) at a dilution of 1:2000 in TSBP buffer (Wani et al., 1996), and reactivity of blotted samples with this antibody was detected using mouse IgG anti-sera conjugated with alkaline phosphatase as described (Kim et al., 1999). Loading of approximately equal numbers of bacteria was confirmed by immunoblotting of duplicate membranes using previously described antisera raised against whole pneumococci (Wani et al., 1996).

Northern Analysis

Total RNA was isolated from O and T variants of strain P303 cells grown to mid-log phase in semi-synthetic medium under atmospheric and anaerobic conditions and purified as described (Weyand et al., 2000). Following separation of RNA on a formamide gel, ethidium bromide stained RNA was photographed and the image was digitized for comparison with RNA size markers. The RNA was transferred to a membrane using the VacuGene™ XL System according to the manufacturer's instructions (Pharmacia LKB Biotechnology, Uppsala, Sweden). The membrane was pre-hybridized in a solution comprising 0.5 molar $NaPO_4$ at pH 7.2, 1.5 millimolar EDTA, and 7% (w/v) SDS for 15 minutes at 65° C. The probe was prepared from an internal fragment of the cps4D gene, and was amplified by PCR using primers having the following sequences:

```
5'-CCGGAATTCG TACAAATATA CAGTTGAGCG GAGATAAAC-3'   (SEQ ID NO:1) and
5'-CGCGGATCCT GTTGCTGTTA CCAAGATGGA CG-3'          (SEQ ID NO:2)
``` and genomic DNA obtained from a type 4 strain. The strain is the same strain used in whole genome sequencing by the Institute for Genomic Research. The PCR product was digested using restriction endonucleases BamHI and EcoRI, and then cloned into a vector having transcriptional terminators flanking the polylinker to allow cloning of streptococcal sequences. This vector was constructed from pJDC9 by insertion of the blunt ended kanamycin resistance cassette of pUK4K (Pharmacia, Upsalla, Sweden) into a blunt ended ClaI site to allow selection of this marker in E. coli (Chen and Morrison, 1988). The cps4D fragment was inserted into BamHI and EcoRI digested vector and transformed into E. coli strain DH5α. Total RNA was extracted from pneumococcal O and T variants of strain P303 grown to mid-log phase in tryptic soy medium under atmospheric and anaerobic conditions.

The results of the experiments presented in this Example are now described.

Selection for Phenotypic Variants in Humans

In order to test whether selection occurs for different pneumococcal phenotypes in carriage and bacteremia in humans, paired isolates of the same serotype were obtained from the nasopharynx and blood of patients who exhibited signs of sepsis. It was necessary to obtain paired isolates, owing to strain-to-strain heterogeneity in colony morphology unrelated to opacity. Pneumococcus could not be isolated from the nasopharynx of bacteremic patients once antibiotic treatment had been initiated. Cultures of the nasopharynx and blood were therefore obtained substantially simultaneously. This limitation required that the study be carried out in a geographic location having a high incidence of pneumococcal bacteremia, in order that a sufficient numbers of paired isolates could be obtained.

Blood and nasopharynx isolates were obtained from 19 adult patients in Blantyre, Malawi, and were only considered as paired isolates if the isolates were subsequently shown to be of the same type by the Quellung reaction using type specific antisera. The majority of the paired isolates were type 1, the most common type in this location, as indicated in Table II. The majority of patients also tested positive for infection with the human immunodeficiency virus, which is believed to account for the high incidence of invasive pneumococcal disease among these patients. Of 19 paired isolates, 17 (89%) were of the T phenotype in the nasopharynx, whereas 12 (63%) were of the O phenotype in the blood. Of the ten paired isolates in which the phenotype of pneumococci obtained from the two sites were discordant, all exhibited a more T-like phenotype in the nasopharynx (P<0.001). This demonstrates that in general there is a selection for phenotypic variants that results in the presence in the blood of a more O-like phenotype derived from among the predominately T-like population in the nasopharynx in natural bacteremic infection.

TABLE II

Opacity Phenotype of Isolates Obtained from Human Carriage and Invasive Infections

| Colony Phenotype | | No. of Patients | Types (No.) | HIV Status | | |
|---|---|---|---|---|---|---|
| Nasopharynx | Blood/CSF[1] | | | + | − | N/A[2] |
| T | T | 7 | 1(4), 4, 18, 19 | 5 | 1 | 1 |
| O | O | 2 | 1(2) | 1 | 0 | 1 |
| O | T | 0 | | | | |
| T | O | 10 | 1(4), 4(2), 6, 12, 15, 22 | 5 | 1 | 4 |

Notes:
[1]4/19 invasive isolates were obtained from cerebrospinal fluid rather than blood.
[2]N/A means clinical status not available.

Effect of Oxygen on Amounts of CPS

Figure 1:
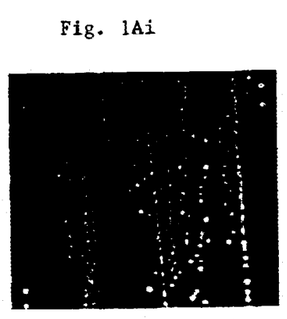
FIG. 1, comprising FIGS. 1Ai–1Avi and 1Bi–1Bvi, is a series of images which indicate the effect of environmental oxygen and carbon dioxide concentration on colony morphology and capsule size, as assessed using the Quellung reaction. Opaque (FIGS. 1Ai, 1Aii, 1Aiii, 1Bi, 1Bii, and 1Biii) and transparent (FIGS. 1Aiv, 1Av, 1Avi, 1Biv, 1Bv, and 1Bvi) variants of a type 6A pneumococcal isolate were grown on T nutrient agar supplemented with catalase for 16 hours at 37° C. under atmospheric conditions (FIGS. 1Ai, 1Aiv, 1Bi, and 1Biv), under atmospheric conditions comprising an increased carbon dioxide concentration (FIGS. 1Aii, 1Av, 1Bii, and 1Bv), and under anaerobic conditions comprising an increased carbon dioxide concentration (FIGS. 1Aiii, 1Avi, 1Biii, and 1Bvi). Colonies in the images in FIGS. 1Ai–1Avi were visualized using oblique, transmitted illumination, and are shown at a magnification of 56×. Capsular material in the images in FIGS. 1Bi–1Bvi were visualized using the Quellung reaction and type specific antisera, and are shown at a magnification of 4000×.

Host and bacterial factors that could promote selection of O variants during infection and T variants during carriage were investigated. It was hypothesized that lower oxygen tension of the sort that would be encountered in consolidated lung would promote a transition to from the T to the O phenotype. Growth of a type 6A clinical isolate, P303, in reduced concentrations of oxygen had no effect on the rate of spontaneous switching from the T- to the O-form. Growth under anaerobic conditions (in the presence of an elevated concentration of carbon dioxide), however, was associated with a shift to a larger and more mucoid colony morphology that was particularly marked for the O variant, as shown in FIG. 1A.

Because pneumococci exhibiting the O phenotype express greater amounts of CPS than those exhibiting the T phenotype, it was considered possible that the greater colony size associated with the O form was a result of increased production of this material (Kim et al., 1998). In initial studies, the refractile zone of CPS surrounding bacterial colonies was visualized using the Quellung reaction and type 6 antisera, as shown in FIG. 1B. This zone was larger for the O variant grown under anaerobic conditions in the presence of 10% carbon dioxide, compared to either growth of the same phenotype in the presence of oxygen or growth of the T variant under any of the conditions tested including the absence of oxygen. In contrast, when the bacteria were cultured under atmospheric conditions, a zone of capsular material could not be detected around colonies of T-form pneumococci. This result confirmed the ability of the O form to synthesize increased quantities of CPS, and indicated that reduced oxygen tension, higher carbon dioxide tension, or both promotes increased CPS production.

Figure 2:
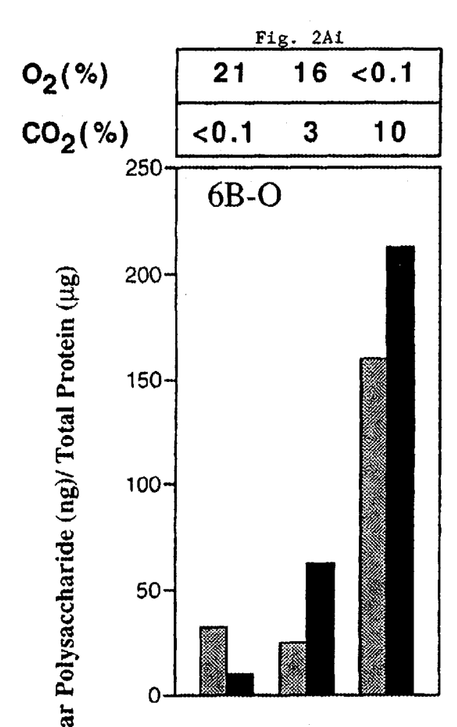

The effect of environmental oxygen and carbon dioxide concentration was assessed quantitatively using an assay developed for measuring amounts of CPS, as indicated in FIG. 2 (Kim et al., 1998). The amounts of CPS per milligram of total cellular protein, as assessed using the capture ELISA described herein, correlated with colony surface area and with capsular volume values calculated based on visualization of zones using the Quellung reaction and with colony surface area, as indicated in Table III. O-form bacteria at either mid-log phase or stationary phase growth exhibited increased amounts of cell-associated CPS compared to the T-form organisms. Growth of the O type 6A variant under anaerobic conditions in the presence of 10% $CO_2$ caused a 7.9-fold rise in the quantity of CPS produced, compared to CPS production in the same cells cultured under atmospheric conditions. Compared to T variants grown under the anaerobic conditions in the presence of 10% $CO_2$, the O variant made 29 times as much CPS. Similar results were obtained using O and T isolates obtained from two unrelated clinical isolates (i.e. using types 6B and 18C).

TABLE III

Characteristics of Pneumococci Grown Under Various Conditions

| | Colony Morphology[3] | | | | | |
|---|---|---|---|---|---|---|
| | O-form | | | T-form | | |
| $O_2$(%) | 21 | 16 | <0.1 | 21 | 16 | <0.1 |
| $CO_2$(%) | <0.1 | 3 | 10 | <0.1 | 3 | 10 |
| Average Colony Area (mm²)[4] | 3.53 | 7.42 | 169 | 1.02 | 5.15 | 12.3 |

TABLE III-continued

Characteristics of Pneumococci Grown Under Various Conditions

|  | Colony Morphology[3] | | | | | |
|---|---|---|---|---|---|---|
|  | O-form | | | T-form | | |
| Volume Occupied by a Single Cell, including Capsule($\mu m^3$)[5] | 3.64 | 6.85 | 63.5 | UD | 4.62 | 10.6 |
| Capsular Polysaccharide (ng/$\mu$g total protein)[6] | 126 | 221 | 997 | 35.4 | 19.4 | 34.2 |

[3]For O and T variants of the same type 6A clinical isolate.
[4]These values are based on colonies observed after 16 hours growth. Values represent the average of determinations made using three single well isolated colonies.
[5]These values are based on capsular material revealed using the Quellung reaction and the formula for the volume of a spherical ellipsoid, $V = (\pi/6)LW^2$. Values represent the average of determinations for three diplococcal forms divided by two to correspond to a single cell. "UD" means that a zone of capsular material was not detectable.
[6]These values are based on capture ELISA assessment of organisms grown in liquid culture at mid-log phase. Values are the mean of two separate determinations.

Production of CPS in culture supernatant was assessed for type 18C pneumococci after growth to stationary phase. The observation that a greater amount of polysaccharide was produced in the culture supernatant of the O-form variant as the concentration of oxygen was decreased and as the concentration of carbon dioxide was increased indicates that increased CPS production was attributable to increased synthesis of CPS by cells under decreased oxygen/increased carbon dioxide conditions, rather than being attributable to decreased release of CPS from cells under increased oxygen/decreased carbon dioxide conditions. A type 9V isolate was used to determine whether increased synthesis of CPS was attributable by decreased oxygen or increased carbon dioxide. Type 9V bacteria grown to stationary phase in the presence of 10% carbon dioxide exhibited 12-fold greater CPS production in the absence of oxygen than the same cells grown in the presence of 10% carbon dioxide and in the presence of oxygen. This confirmed that the oxygen tension, rather than carbon dioxide tension, is the predominant environmental factor affecting the degree of CPS production.

Changes in CPS Production Correlate with Changes in cpsD/CpsD

The next phase of the study addressed the mechanism by which the effect of oxygen on CPS production is mediated. Involvement of a two-component signal transduction system for sensing and transducing oxygen tension/presence was examined. Previously described marked mutations in 11 of the 12 of two-component signal transduction systems found in the genome of a type 3 isolate of were transformed into strain P303, as described (Throup et al., 2000). 10 constructs harboring mutations in response regulator homologues were made, as were 7 constructs harboring mutations in histidine kinase homologues. For each of the 17 mutant homologues tested in P303, there was no effect on increased colony size or zone of capsule formation, as assessed using the Quellung reaction, in experiments in which the cells were grown under anaerobic conditions. This result indicated that it is unlikely that the effect of oxygen is mediated through a TCSTS, although one of these systems in the pneumococcus could not be examined because the genes appear to be essential.

The genes in a locus known to be required for expression of CPS were examined next. Since the effect of oxygen on amounts of CPS was observed in strains of multiple types, genes conserved among different types were considered the most likely candidates. Among the genes in the capsule loci, only the first four, cpsA-D, are common to pneumococci of different types (Iannelli et al., 1999). Type 3 pneumococci are known to form mucoid colonies and to have large capsules, as assessed by the Quellung reaction, when grown under atmospheric conditions, as indicated in Table I (Knecht et al., 1970). Unlike all other pneumococcal types tested, type 3 strains failed to show an increase in the sizes of colonies or capsules when cultured under anaerobic conditions, relative to the sizes when cultured under atmospheric conditions. Based on this observation, differences in cpsA-D between the type 3 and loci of other types was determined.

Homologs of cpsA, encoding a putative transcriptional attenuator, and cpsB, encoding a protein of unknown function, are present in the type 3 capsulation locus (Genbank accession no. Z47210; Arrecubieta, 1995). The gene encoding CpsC in serotype 2 pneumococci is highly conserved in the type 3 capsulation locus, but the predicted CpsD in serotype 3 pneumococci is truncated following amino acid 69 (of 226). CpsC and CpsD are required for expression of the pneumococcal capsule and together they are homologous to a single protein (Wzc) expressed in *Escherichia coli* that is involved in chain length regulation and export of the extracellular polysaccharide designated colanic acid (Morona et al., 1999; Stevenson et al., 1996).

In *E. coli*, Wzc undergoes reversible autophosphorylation at a tyrosine residue (Vincent et al., 1999). A monoclonal antibody which is designated 4G10 which binds specifically with phosphorylated tyrosine residues was used to determine by Western analysis that phosphorylated tyrosine is present in the pneumococcus. A single band of approximately 26 kD, the predicted size of CpsD, was present in whole cell lysates of the type 6A isolate. A single band of the same size was also seen in whole cell lysates of the types 6B, 18C, and 9V strains used in this study, but was absent from the type 3 pneumococci (which have a truncated CpsD). These observations indicated that CpsD is phosphorylatable at a tyrosine residue. Further evidence that 4G10 was recognizing CpsD having a phosphorylated tyrosine residues was obtained by comparing strains D39 (an non-encapsulated mutant) and R6x (a strain having a 7504 base pair deletion spanning cps2A–H, of which only A–D are common to other types; Iannelli et al., 1999). The mutation in R6x-type pneumococci was corrected in some experiments by transforming the bacteria using DNA obtained from either the (type 2) D39 parent strain or a type 3 strain to yield an encapsulated strain with either type 3 or 2 capsule in the D39 type 2 genetic background.

Failure of 4G10 to react with R6x and the type 3 R6x transformant and reaction of the antibody with the type 2 R6x transformant confirmed that expression of the protein corresponding to this band requires one of the first four common genes in the capsulation locus and an intact copy of cpsD. It was determined that the 4G10 reactive protein is not likely to be CpsA or B based on size. There are only 15 conservative amino acid changes between type 2 and 3 CpsC, of which none involve tyrosine. The lack of the 4G10 reactive band in the type 3 strain indicated that the 4G10-reactive protein is not CpsC. It was therefore concluded that CpsD protein comprises a phosphorylatable tyrosine residue in the pneumococcus.

Figure 3A:
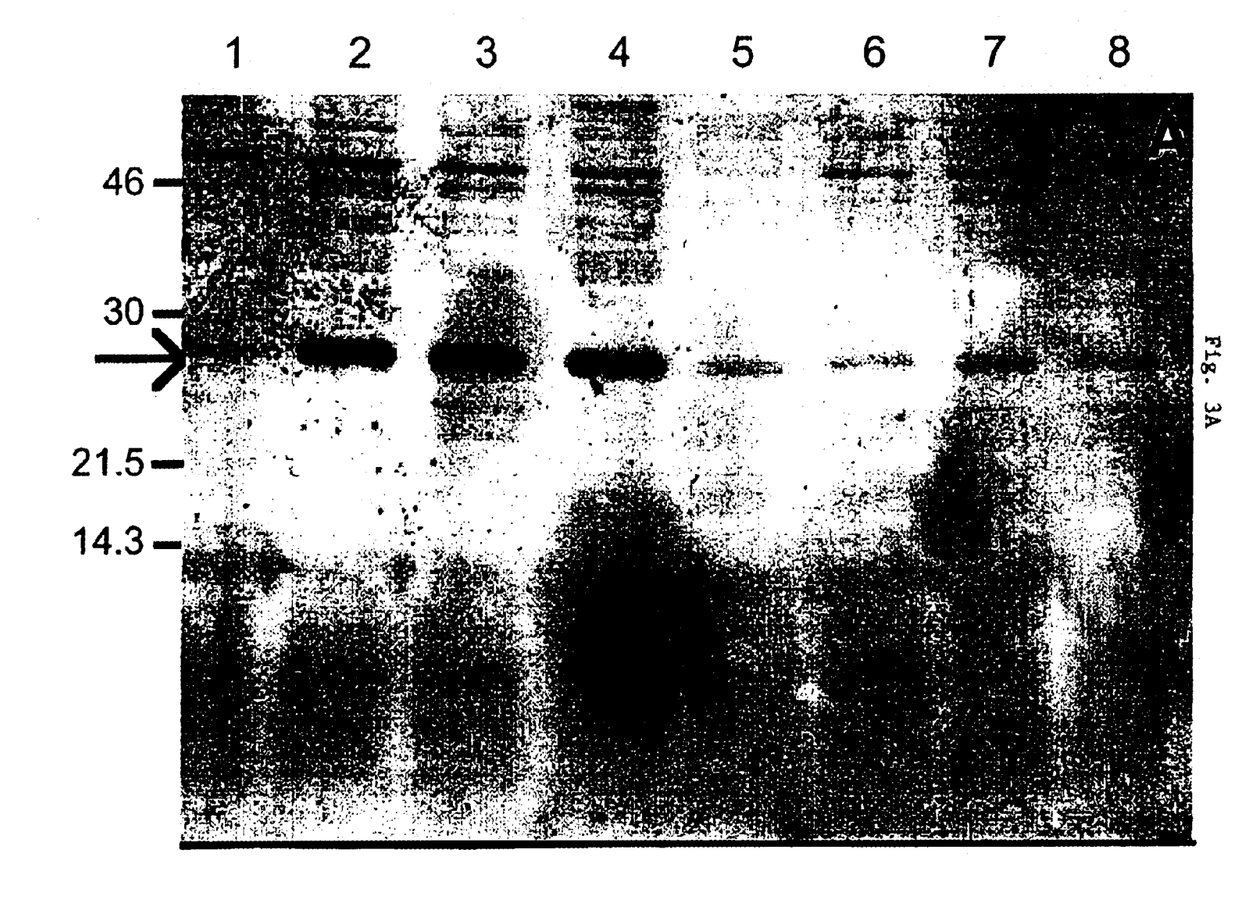
Figure 3B:
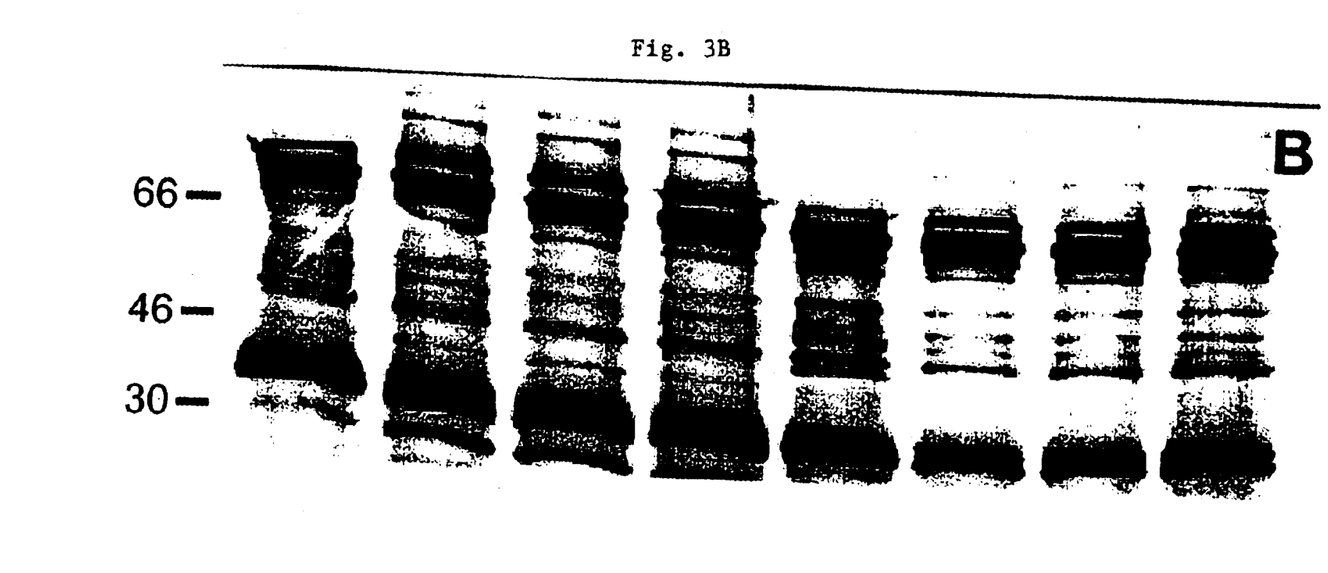

The effect of growth under various concentrations of oxygen and carbon dioxide on tyrosine phosphorylation of CpsD was examined. Lysates of whole cells of the O and T forms of the type 6A pneumococcal isolate designated P303 which had been grown under various concentrations of oxygen and carbon dioxide were adjusted to an equivalent density and examined by Western analysis using the phosphotyrosine-specific monoclonal antibody 4G10. The results of these experiments are shown in FIG. 3. A single band of the expected size for CpsD was detected in the O variant grown in the presence of oxygen. There was no reactivity with the extract obtained from an approximately equal number of cells grown anaerobically, as indicated in lane 1 of FIG. 3. There was no apparent effect of differences in carbon dioxide tension from <0.1 to 10%, as indicated by the results in lanes 2–4 of FIG. 3. Under all conditions tested (oxygen <0.1% to 21% and carbon dioxide <0.1% to 10%), reactivity of the antibody with cell extracts of the T variant was faint. Similar results were obtained using other strains. It was therefore concluded that tyrosine phosphorylation of CpsD is affected by opacity phenotype and requires growth in the presence of oxygen.

Difference in tyrosine phosphorylation can affect the activity of CpsD and account for decreased expression of CPS in O pneumococci in the presence of oxygen. Neither O nor T pneumococci grown anaerobically express phosphorylated tyrosine; however the two phenotypic forms exhibit large differences in the degree of CPS production.

Figure 4:
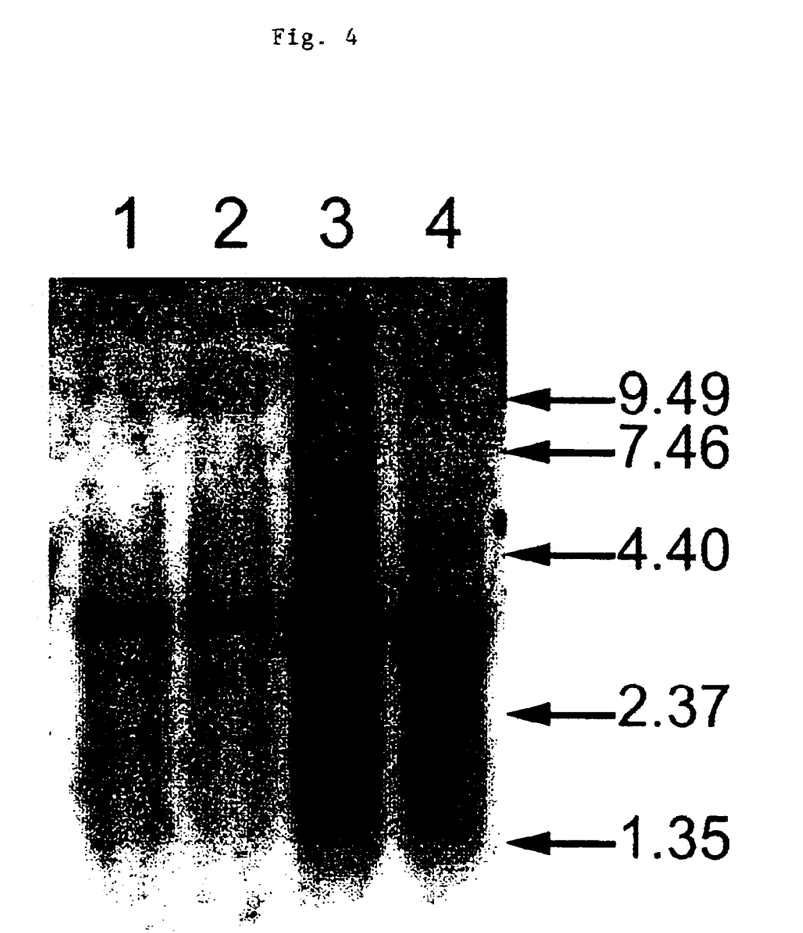
FIG. 4 is an image which depicts the effects of environmental oxygen and carbon dioxide concentrations and opacity phenotype on transcription of cpsD, as assessed by Northern analysis. Total RNA obtained from O (Lanes 1 and 2) or T (Lanes 3 and 4) forms of pneumococcal variant P303 was separated on a formamide gel and probed using a radio-labeled fragment of cpsD obtained from a serotype 4 pneumococcus. Bacteria from which RNA was isolated were grown under <0.1% $O_2$/10% $CO_2$ (Lanes 1 and 3) or under 21% $O_2$/<0.1% $CO_2$ (Lanes 2 and 4). Size markers are RNA standards in kilodaltons.

Northern analysis was used to determine if differences between O and T variants were due to differences in the level of transcription of cpsD. The results of these experiments are shown in FIG. 4. Total cellular RNA was obtained from O and T forms of pneumococcal strain P303 grown either under atmospheric conditions or anaerobically in the presence of 10% carbon dioxide. The RNA was probed using a cloned fragment of cpsD. Quantitative differences in transcriptional activity were determined by assessing hybridization of radio-labeled probe with cpsD in mRNA and adjusting these values for the total amount of RNA present in the hybridization assay mixture. These experiments demonstrated that oxygen concentration had no substantial effect on the level of cpsD transcription. However, cpsD was transcribed at a 3.4-fold greater level in T-form cells, relative to O-form cells. It was therefore concluded that transcriptional regulation of cpsD determines the opacity phenotype of pneumococci.

Without wishing to be bound by any particular theory of operation, it is believed that CpsD regulates CPS production. Correlation between differences observed in the degree of tyrosine phosphorylation of CpsD and differences in CPS production support this theory. It is believed that CpsD functions as a tyrosine kinase, based in part on its amino acid sequence similarity to a tyrosine autophosphorylating enzyme in *E. coli* which is involved in chain length regulation and export of the extracellular polysaccharide colanic acid. Cps23FD has 30% identity and 49% similarity over 188 of 229 amino acids to Wzc. CpsD of serotype 23f pneumococcus contains an unusual carboxyl-terminal amino acid sequence (YGSYGNYGNY GKNKK; SEQ ID NO: 3) which contains a repetitive feature $(YGX)_4$ including tyrosine residues. This carboxyl-terminal region exhibits considerably greater amino acid sequence heterogeneity among pneumococcal variants than the remainder of CpsD. It is believed that the variability in CPS production among pneumococcal strains is attributable to the variability of this carboxyl-terminal portion among the strains, the sequence variation affecting the phosphorylat-ability of the protein. A number of other bacterial protein kinases have been identified and these have in common a C-terminus with a tyrosine-rich repetitive feature (Ilan et al., 1999). Inability to generate a pneumococcal strain harboring a mutation in cpsD while maintaining the ability of the strain to produce CPS is further evidence of the importance of this gene in CPS and capsule production.

The following model of a mechanism for regulating CPS production in response to colony opacity phenotype and oxygen tension is proposed. The model involves transcriptional regulation of cpsD and post-translational modification of CpsD.

CpsD is a negative regulatory factor which act on genes involved in biosynthesis of pneumococcal type-specific CPS. Relatively low cpsD transcription accounts for the relatively high amounts of CPS expressed in O-type pneumococci under anaerobic conditions. Apart from transcriptional regulation of cpsD, which accounts for a significant proportion of CPS expression regulation, a second level of regulation is involved, namely phosphorylation or autophosphorylation of tyrosine residue(s) on CpsD. Phosphorylation of CpsD affects only the O variant and requires growth under aerobic conditions. Detectability of CpsD which is phosphorylated at one or more tyrosine residues only in the O variant may be due to increased phosphatase activity in T pneumococci. Tyrosine phosphorylation increases the negative regulatory activity of CpsD, such that phosphorylated CpsD decreases synthesis of CPS under aerobic conditions. As a result, less CPS is made by O variants under aerobic conditions than under anaerobic growth conditions. Relatively low CPS production in T-form pneumococci, even in the absence of appreciable tyrosine phosphorylation of CpsD, is attributable to increased expression of cpsD in T-form pneumococci.

What had previously been described as improved growth under anaerobic condition, may in fact be an effect of increased CPS synthesis resulting in larger colony size (Modde, 1978).

Homologues of CpsD with even greater similarity to Wzc are present in many other species of bacteria that express surface polysaccharides. Examples of such species include *Streptococcus agalactiae, Staphylococcus aureus, Klebsiella pneumoniae,* and *Acinetobacter johnsonii.* Since capsules and their size are critical determinants of virulence, the ability to regulate amounts of CPS based on transcriptional and post-translation modification of this class of gene/protein may be important in facilitating the ability of encapsulated bacteria to adapt to the differing requirements of colonization and infection.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. In a method of producing capsular polysaccharide from a pneumococcus by maintaining the pneumococcus in a growth medium, the improvement comprising maintaining a gas having a sub-atmospheric concentration of oxygen in contact with the growth medium.

2. The improvement of claim 1, wherein the gas has an oxygen concentration not greater than about 16%.

3. The improvement of claim 2, wherein the gas has an oxygen concentration not greater than about 0.1%.

4. The improvement of claim 1, wherein the pneumococcus is an organism of the genus Streptococcus.

5. The improvement of claim 4, wherein the pneumococcus is an organism of the species *Streptococcus pneumoniae*.

6. The improvement of claim 5, wherein the pneumococcus is a variant of the species *Streptococcus pneumoniae* selected from the group consisting of variants 6A, 6B, 18C, and 9V.

7. In a method of producing capsular polysaccharide from a pneumococcus by maintaining the pneumococcus in a growth medium, the improvement comprising maintaining a gas having a super-atmospheric concentration of carbon dioxide in contact with the growth medium.

8. The improvement of claim 7, wherein the gas has a carbon dioxide concentration of at least about 3%.

9. The improvement of claim 8, wherein the gas has a carbon dioxide concentration of at least about 10%.

10. The improvement of claim 7, wherein the gas has a sub-atmospheric concentration of oxygen.

11. A method of alleviating a pneumococcal infection in an animal, the method comprising maintaining the animal in contact with a gas having a super-atmospheric concentration of oxygen.

12. The method of claim 11, wherein the lungs of the animal are maintained in contact with the gas.

13. The method of claim 11, wherein the gas has an oxygen concentration of at least about 25%.

14. The method of claim 13, wherein the gas has an oxygen concentration of at least about 50%.

15. The method of claim 14, wherein the gas is substantially pure oxygen.

16. The method of claim 11, wherein the infection is selected from the group consisting of pneumonia, bacteremia, sepsis, and meningitis.

17. A method of making an immunogenic preparation for administration to an animal at risk for developing a pneumococcal infection, the method comprising maintaining pneumococcal cells in a growth medium having an oxygen content lower than the same medium equilibrated at the same temperature with normal air; and isolating capsular polysaccharide produced by the cells from the cells, whereby the isolated polysaccharide constitutes the immunogenic preparation.

18. In a method of producing capsular polysaccharide from a pneumococcus by maintaining the pneumococcus in a growth medium, the improvement comprising maintaining the carbon dioxide concentration of the growth medium at a level at least equal to the concentration of carbon dioxide in the same growth medium equilibrated at the same temperature with a gas comprising 5% carbon dioxide.

19. A method of producing pneumococcal polysaccharide, the method comprising maintaining pneumococcal cells in a growth medium having an oxygen content lower than the same medium equilibrated at the same temperature with normal air.

20. The method of claim 19, wherein the medium is substantially devoid of oxygen.

21. The method of claim 19, wherein the medium has a carbon dioxide content which is greater than the same medium equilibrated at the same temperature with normal air.

22. The method of claim 21, wherein the medium is saturated with carbon dioxide.

23. The method of claim 21, wherein the medium comprises a carbonate or bicarbonate salt.

24. A method of assessing whether a test compound is useful for alleviating a pneumococcal infection in an animal, the method comprising comparing the degree of phosphorylation of CpsD in pneumococcal cells maintained in the presence of the test compound and the degree of phosphorylation of CpsD in the same type of cells maintained in the absence of the test compound, wherein if the degree of phosphorylation of CpsD in the cells maintained in the presence of the test compound is less than the degree of phosphorylation of CpsD in the cells maintained in the absence of the test compound, then the test compound is useful for alleviating the infection.

25. The method of claim 24, wherein the degree of phosphorylation of CpsD is assessed by assessing the number of phosphorylated tyrosine residues present in CpsD.

26. The method of claim 24, wherein the degree of phosphorylation of CpsD is assessed by assessing the fraction of CpsD having at least one phosphorylated tyrosine residue.

* * * * *

(12) EX PARTE REEXAMINATION CERTIFICATE (7436th)
United States Patent
Weiser (10) Number: US 6,642,017 C1
(45) Certificate Issued: Mar. 30, 2010

(54) MODULATING PRODUCTION OF PNEUMOCOCCAL CAPSULAR POLYSACCHARIDE

(75) Inventor: Jeffrey N. Weiser, Merion, PA (US)

(73) Assignee: The Children's Hospital of Philadelphia, Philadelphia, PA (US)

Reexamination Request:
No. 90/007,868, Jan. 10, 2006

Reexamination Certificate for:
Patent No.: 6,642,017
Issued: Nov. 4, 2003
Appl. No.: 09/831,184
Filed: Jan. 30, 2002

(22) PCT Filed: Mar. 16, 2001

(86) PCT No.: PCT/US01/08442

§ 371 (c)(1),
(2), (4) Date: Jan. 30, 2002

(87) PCT Pub. No.: WO01/68903

PCT Pub. Date: Sep. 20, 2001

Related U.S. Application Data

(60) Provisional application No. 60/189,847, filed on Mar. 16, 2000.

(51) Int. Cl.
*C12N 1/20* (2006.01)
*C12P 19/00* (2006.01)
*C12P 19/04* (2006.01)
*C12Q 1/18* (2006.01)

(52) U.S. Cl. .............................. 435/34; 435/4; 435/29; 435/36

(58) Field of Classification Search ......................... None
See application file for complete search history.

(56) References Cited

U.S. PATENT DOCUMENTS 5,948,900 A  9/1999 Yother

FOREIGN PATENT DOCUMENTS

GB        2102291       7/1985
WO     WO 200168903    9/2001

OTHER PUBLICATIONS

John E. Martin et al., New System for Cultivation of Neisseria gonorrhoeae, 27 Amn. Soc'y for Microbiology (No. 4) 802.*

Morona, J.K., et al., "Tyrosine phosphorylation of CpsD negatively regulates capsular polysaccharide biosynthesis in Streptococcus pneumoniae," Mol. Microbiol., 35(6): 1431–1442, (2000).

Nielsen, S. V., et al., "Incidence of Invasive pneumococcal disease and distribution of capsular types of pneumococci in Denmark, 1989–94," Epidemiol. Infect., 117(3):411–6, (Dec. 1996). [Abstract].

Brogan, O., et al., "Evaluation of anaerobic culture and effect of culture medium supplementation with factor V on colonial morphology and efficacy of isolation of Streptococcus pneumoniae from sputum," J. Clin. Pathol., 40:368–371, (1987).

Howden, R., "Use of anaerobic culture for the improved isolation of Streptocuccus pneumoniae," J. Clin. Path., 29:50–53, (1976).

Kempner and Schlaer "Effect of $CO_2$ on the Growth Rate of the Pneumococcus" Journal of Bacteriology 43(3):387–396 (1942).

Kim et al., "Optimization of Culture Conditions for Production of Pneumococcal Capsular Polysaccharide Type I" Journal of Microbiology 34(2):179–183 (1996).

Dillard and Yother "Analysis of Streptococcus pneumoniae Sequences Cloned into Escherichia coli: Effect of Promoter Strength and Transcription Terminators" Journal of Bacteriology 173(16): 5105–5109 (1991).

Chen and Morrison, "Construction and properties of a new insertion vector, pJDC9, that is protected by transcriptional terminators and useful for cloning of DNA from streptococcus pneumoniae." Gene 64: 155–164 (1988).

Auzat et al., "The NADH oxidase of Streptococcus pneumoniae: its involvement in competence and virulence." Molecular Microbiology 34(5): 1018–1028 (1999).

Arrecubieta et al., "Sequence and transcriptional analysis of a DNA region involved in the production of capsular polysaccharide in Streptococcus pneumoniae type 3." Gene 167: 1–7 (1995).

Modde, "Etude de l'influence de la tension d'$O_2$ de $CO_2$ et de l'anaerobiose sur la morphologie et le nombre des colonies de pneumocoque—influence of $C_2$ –,$CO_2$ —tension and anaerobiosis upon number and morphology of pneumococcal colonies." Experientia 34/10: 1285–1286 (1978).

Avery et al., "The Protective Action of a Specific Enzyme Against Type III Pneumococcus Infection in Mice." The Journal of Experimental Medecine 54: 73–90 (1931).

Knecht et al., "Some Biological Properties of Pneumococcus Type 37 and the Chemistry of its Capsular Polysaccharide." Journal of Experimental Medicine 132: 475–487 (1970).

Avery et al., "Studies on the Chemical Nature of the Substance Inducing Transformation of Pneumococcal Types." Journal of Experimental Medicine 79(1):137–157 (1944).

MaCleod et al., "relation of virulence of pneumococcal strains for mice to the quantity of capsular polysaccharide formed in vitro." Journal of Experimental Medicine 92:1–9 (1950).

(Continued)

*Primary Examiner*—Dwayne C Jones (57) ABSTRACT

The invention relates to methods of modulating capsular polysaccharide production in pneumococci such as *Streptococcus pneumoniae*. The invention further relates to methods of alleviating pneumococcal infections in animals, and to methods of identifying both agents capable of modulating pneumococcal capsular polysaccharide biosynthesis and agents useful for alleviating pneumoccal infections in animals.

OTHER PUBLICATIONS

Caparon et al., "Environmental Regulation of Virulence in Group A Streptococci: Transcription of the Gene Encoding M Protein Is Stimulated by Carbon Dioxide." Journal of Bacteriology: 5693–5701 (1992).

Weiser "Phase Variation in Colony Opacity by Streptococcus pneumoniae." Microbial Drug Resistance 4(2): 129–135 (1998).

Weiser and Kapoor "Effect of Instrastrain Variation in the Amount of Capsular Polysaccharide on Genetic Transformation of Streptococcus pneumoniae: Implications for Virulence Studies of Encapsulated Strains." Infection and Immunity: 3690–3692 (1999).

Watson and Musher "Interruption of Capsule Production in Streptococcus pneumoniae Serotype 3 by Insertion of Transposon Tn916." Infection and Immunity 58(9): 3135–3138 (1990).

Weiser et al., "Phase Variation in Pneumococcal Opacity: Relationship between Colonial Morphology and Nasopharyngeal Colonization." Infection and Immunity 62(6): 2582–2589 (1994).

Gibson et al., "Group B Streptococci Invade Endothelial Cells: Type III Capsular Polysaccharide Attenuates Invasion." Infection and Immunity 61(2): 478–485 (1993).

St. Geme and Falkow "Low of Capsule Expression by Haemophilus influenzae Type b Results in Enhanced Adherence to and Invasion of Human Cells." Infection and Immunity 59(4): 1325–1333 (1991).

Kim et al., "Relationship between Cell Surface Carbohydrates and Intrastrain Variation on Opsonophagocytosis of Streptococcus pneumoniae." Infection and Immunity 67(5): 2327–2333 (1999).

Tuomanen et al., "Pathogenesis of Pneumococcal Infection." The New England Journal of Medicine 332(19): 1280–1284 (1995).

Saluja and Weiser "The genetic basis of colony opacity in Streptococcus pneumoniae: evidence for the effect of box elements on the frequency of phenotypic variation." Molecular Microbiology 16(2): 215–227 (1995).

Sellin et al., "Phase-shift of polysaccharide capsule expression in group B streptococci, type III." Microbial Pathogenesis 18:401–415 (1995).

Ring et al., "Pneumococcal Trafficking across the Blood–Brain Barrier Molecular Analysis of a Novel Bidirectional Pathway." J. Clin. Invest. 102(2): 347–360 (1998).

Iannelli et al., "The Type 2 Capsule Locus of Streptococcus pneumoniae." Journal of Bacteriology 181(8):2652–2654 (1999).

Levin and Wessels "Identification of csrR/csrS, a genetic locus that regulates hyaluronic acid capsule synthesis in group A Streptococcus." Molecular Microbiology 30(1): 209–219 (1998).

Ilan et al., "Protein tyrosine kinases in baterial pathogens are associated with virulence and production of exopolysaccharide." The EMBO Journal 18(12): 3241–3248 (1999).

Vincent et al., "Cells of Escherichia coli Contain a Protein–Tyrosine Kinase, Wzc, and a Phosphotyrosine–Protein Phosphatase, Wzb." Journal of Bacteriology 181(11): 3472–3477 (1999).

Throup et al., "A genomic analysis of two–component signal transduction in Streptococcus pneumoniae." Molecular Microbiology 35(3): 566–576 (2000).

Rosenow et al., "Contribution of novel choline–binding proteins to adherence, colonization and immunogenicity of Streptococcus pneumoniae." Molecular Microbiology 25(5): 819–829 (1997).

Raz et al., "Pneumococcal Bacteremia in Hospitalized Israeli Adults: Epidemiology and Resistance to Penicillin." Clinical Infectious Diseases 24: 1164–8 (1997).

Kim and Wesier "Association of Intrastrain Phase Variation in Quantity of Capsular Polysaccharide and Teichoic Acid with the Virulence of Streptococcus pneumoniae." The Journal of Infectious Diseases 177: 367–77 (1998).

Schrager et al., "Hyaluronic Acid Capsule and the Role of Streptococcal Entry into Keratinocytes in Invasive Skin Infection." J. Clin. Invest. 98(9): 1954–1958 (1996).

Wani et al., "Identification, Cloning, and Sequencing of the Immunoglubin A1 Protease Gene of Streptococcus pneumoniae." Infection and Immunity: 3967–3974 (1996).

Stevenson et al., "Organization of the Escherichia coli K–12 Gene Cluster Responsible for Production of the Extracellular Polyssaccharide Colanic Acid." Journal of Bacteriology: 4885–4893 (1996).

Hammerschmidt et al., "Capsule phase variation in Neisseria meningitidis serogroup B by slipped–strand mispairing in the polysialytransferase gene (siaD): correlation with bacterial invasion and the outbreak of meningococcal disease." Molecular Microbiology 20(6): 1211–1220 (1996).

Cundell et al., "Streptococcus pneumoniae anchor to activated human cells by the receptor for platelet–activating factor." Nature 377: 435–438 (1995).

Austrian and Collins "Importance of Carbon Dioxide in the Isolation of Pneumococci." Journal of Bacteriology 92(5): 1281–1284 (1996).

Tomasz "Studies on the Competence (for genetic transformation) of Diplococcus pheumoniae in a Synthetic Medium" Bacteriol. Proc. 64: 29 G87 (1964).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 24–26 is confirmed.

Claims 2, 8, and 11–16 are cancelled.

Claims 1, 3–7, 9, 10 and 17–23 are determined to be patentable as amended.

New claims 27–35 are added and determined to be patentable.

1. [In a] *A* method of producing capsular polysaccharide from a pneumococcus[by], *said method comprising:*
   a) *obtaining an opaque variant of the pneumococcus and*
   b) maintaining *said opaque variant of* the pneumococcus in a growth medium[, the improvement comprising maintaining] *in contact with* a gas having [a sub-atmospheric concentration of oxygen in contact with the growth medium] *an oxygen concentration less than about 16%, said method optionally comprising isolating the produced capsular polysaccharide*.

3. The [improvement] *method* of claim [2] *1*, wherein [the] *said* gas has an oxygen concentration not greater than about 0.1%.

4. The [improvement] *method* of claim 1, wherein [the] *said* pneumococcus is an organism of the genus Streptococcus.

5. The [improvement] *method* of claim 4, wherein [the] *said* pneumococcus is an organism of the species Streptococcus pneumoniae.

6. The [improvement] *method* of claim 5, wherein [the] *said* pneumococcus is a variant of the species Streptococcus pneumoniae selected from the group consisting of variants 6A, 6B, 18C, and 9V.

7. [In a] *A* method of producing capsular polysaccharide from a pneumococcus [by], *said method comprising obtaining an opaque variant of the pneumococcus and* maintaining *said opaque variant of* the pneumoccus in a growth medium[, the improvement comprising maintaining] *in contact with* a gas having a [super-atmospheric concentration of carbon dioxide in contact with the growth medium] *carbon dioxide concentration greater than about 5%, said method optionally comprising isolating the produced capsular polysaccharide*.

9. The [improvement] *method* of claim [8] *7*, wherein [the] *said* gas has a carbon dioxide concentration of at least about 10%.

10. The [improvement] *method* of claim 7, wherein [the] *said* gas has a sub-atmospheric concentration of oxygen.

17. A method of making an immunogenic preparation for administration to an animal at risk for developing a pneumococcal infection, the method comprising *the steps of:*
   a) *obtaining an opaque variant of the pneumococcus;*
   b) maintaining [pneumococcal cells] *said opaque variant of the pneumococcus* in a growth medium having an oxygen content lower than the same medium equilibrated at the same temperature with normal air *having an oxygen concentration less than 16%*; and
   c) isolating capsular polysaccharide produced by the cells from the cells; whereby the isolated polysaccharide constitutes the immunogenic preparation.

18. [In a] *A* method of producing capsular polysaccharide from a pneumococcus [by], *said method comprising obtaining an opaque variant of the pneumococcus and* maintaining said opaque variant of the pneumococcus in a growth medium, [the improvement comprising maintaining] *wherein* the carbon dioxide concentration of [the] *said* growth medium [at a level at least equal to] *is greater than* the concentration of carbon dioxide in the same growth medium equilibrated at the same temperature with a gas comprising 5% carbon dioxide.

19. A method of producing pneumococcal polysaccharide, [the] *said* method comprising *obtaining an opaque variant of a pneumococcus and* maintaining [pneumococcal cells] *said pneumococcus* in a growth medium having an oxygen content lower than the same medium equilibrated at the same temperature with normal air *which has an oxygen content of 16%*.

20. The method of claim 19, wherein [the] *said* growth medium is substantially devoid of oxygen.

21. The method of claim 19, wherein [the] *said* growth medium has a carbon dioxide content which is greater than the same medium equilibrated at the same temperature with normal air.

22. The method of claim 21, wherein [the] *said* growth medium is saturated with carbon dioxide.

23. The method of claim 21, wherein [the] *said* growth medium comprises a carbonate or bicarbonate salt.

*27. The method of claim 1, wherein said gas has a super atmospheric concentration of carbon dioxide.*

*28. The method of claim 10, wherein said gas has an oxygen concentration not greater than about 0.1%.*

*29. The method of claim 17, wherein said gas has an oxygen concentration not greater than about 0.1%.*

*30. The method of claim 17, wherein said gas has a super atmospheric concentration of carbon dioxide.*

*31. The method of claim 19, wherein said gas has an oxygen concentration not greater than about 0.1%.*

*32. The method of claim 1, wherein said opaque variant of the pneumococcus in step a) is obtained from a sample of pneumococcus comprising transparent and opaque variants.*

*33. The method of claim 32, wherein said opaque variant is selected from said sample prior to performing step b).*

*34. The method of claim 32, wherein said sample is obtained from blood.*

*35. The method of claim 32, wherein said sample is obtained from the nasopharynx.*

* * * * *